United States Patent [19]
Hoffmann

[11] Patent Number: 6,110,488
[45] Date of Patent: Aug. 29, 2000

[54] TRANSDERMAL THERAPEUTIC SYSTEM, ITS USE AND PRODUCTION PROCESS

[75] Inventor: Annegrete Hoffmann, Neuwied, Germany

[73] Assignee: LTS Lohmann Therapie-Systeme GmbH & Co. KG, Neuwied, Germany

[21] Appl. No.: 08/471,021

[22] Filed: Jun. 6, 1995

Related U.S. Application Data

[62] Continuation-in-part of application No. 08/344,415, Nov. 23, 1994, abandoned, which is a continuation of application No. 08/027,822, May 7, 1993, abandoned, which is a division of application No. 07/908,930, Jul. 8, 1992, abandoned, which is a continuation of application No. 07/597,102, Oct. 12, 1990, abandoned, which is a continuation of application No. 07/219,066, filed as application No. PCT/DE87/00372, Aug. 20, 1987.

[30] Foreign Application Priority Data

Aug. 28, 1986 [DE] Germany ............................ 36 29 304

[51] Int. Cl.[7] ........................................ A61F 13/00
[52] U.S. Cl. ........................... 424/449; 424/447; 424/448
[58] Field of Search ....................... 424/447, 448, 424/449

[56] References Cited

U.S. PATENT DOCUMENTS

| | | | |
|---|---|---|---|
| 3,598,123 | 8/1971 | Zaffaroni | 424/435 |
| 3,731,683 | 5/1973 | Zaffaroni | 424/434 |
| 3,797,494 | 3/1974 | Zaffaroni | 424/434 |
| 4,286,592 | 9/1981 | Chandrasekaran | 424/449 |
| 4,314,557 | 2/1982 | Chandrasekaran | 424/448 |
| 4,379,454 | 4/1983 | Campbell et al. | 424/448 |
| 4,435,180 | 3/1984 | Leeper | 424/402 |
| 4,597,961 | 7/1986 | Etscorn | 424/448 |
| 4,615,699 | 10/1986 | Gale | 424/448 |
| 4,690,683 | 9/1987 | Chien | 424/448 |
| 4,699,792 | 10/1987 | Nick et al. | 424/446 |
| 4,719,226 | 1/1988 | Otsuka et al. | 424/449 |
| 4,769,028 | 9/1988 | Hoffmann et al. | 424/443 |
| 4,784,857 | 11/1988 | Berry et al. | 424/449 |
| 4,915,950 | 4/1990 | Miranda et al. | 424/448 |
| 4,933,184 | 6/1990 | Tsuk | 424/449 |
| 5,077,104 | 12/1991 | Hunt et al. | 428/34.3 |
| 5,268,209 | 12/1993 | Hunt et al. | 428/34.3 |
| B1 3,598,122 | 11/1982 | Zaffaroni | 424/435 |

FOREIGN PATENT DOCUMENTS

| | | |
|---|---|---|
| 565178 | 7/1985 | Australia . |
| 117027 | 1/1984 | European Pat. Off. . |
| 0 416 842 | 3/1991 | European Pat. Off. . |
| 21 35 533 | 2/1973 | Germany . |
| 34 24 837 | 7/1984 | Germany . |
| 34 38 284 | 10/1984 | Germany . |
| 1 361 289 | 6/1971 | United Kingdom . |
| WO85/05036 | 4/1985 | WIPO . |

OTHER PUBLICATIONS

Article from Kunstatoffe Plastics, Sep. 1974 (pp. 13–20), 1974.

*Primary Examiner*—Jyothsna Venkat
*Attorney, Agent, or Firm*—Peter S. Gilster

[57] ABSTRACT

A therapeutic system for supplying active substances to the skin consists of a backing layer remote from the skin, with at least one active substance depot. The depot may consist of a fluid active substance or a fluid composition comprising an active substance delivery control matrix. There is also included an adhesive fixing device for fixing the therapeutic system on the skin. The therapeutic system is characterized in that the active substance depots (14) consist of at least one adjuvant having a supporting and distributing function by being provided with a planar textile material completely surrounded by matrix (12).

21 Claims, 2 Drawing Sheets ps.com/patents/US6110488
TRANSDERMAL THERAPEUTIC SYSTEM, ITS USE AND PRODUCTION PROCESS This is a continuation-in-part of Ser. No. 08/344,415 filed Nov. 23, 1994 now abandoned, which is a continuation of application Ser. No. 08/027,822 filed May 7, 1993, now abandoned, which is a division of application Ser. No. 07/908,930, filed Jul. 8, 1992, now abandoned, which is a continuation of application Ser. No. 07/597,102, filed Oct. 12, 1990, now abandoned, which is a continuation of application Ser. No. 07/219,066, filed Jun. 27, 1988, now abandoned, which is a 371 of PCT application number DE87/00372 filed Aug. 20, 1987.

FIELD OF THE INVENTION

The invention relates to a therapeutic system for applying active substances. to the skin, with a backing layer remote from the skin, at least one active substance depot, an active substance distribution device which is linked with the active substance depot, an active substance delivery control device controlling the delivery of the active substance through the system and a pressure sensitive adhesive fixing device for the therapeutic system on the skin, its use and process for the production thereof.

BACKGROUND OF THE INVENTION

Therapeutic systems for the transdermal administration of medicaments supply one or more active substances at a predetermined rate and in continuous manner over a fixed period to a given application point on the skin.

These systems are therapeutic precision instruments ensuring a continuous active substance release.

Such therapeutic systems can have both a topical and a systemic action and the large number of active substances which can be applied in this way and their different chemical, physical and pharmacological characteristics make ever new demands on the production of such systems.

Conventionally these transdermal systems have at least one active substance reservoir, where the active substance is present in solid, liquid or disperse molecular form and an adhesion layer through which the system is closely connected with the skin and through which active substance transfer takes place, a control membrane and protective/covering layers which are substantially impermeable for the active substance.

The known systems are difficult to manufacture and have a complicated structure.

One problem of conventional systems is that of being able to process readily volatile active substances, because the evaporation of the active substance is difficult to control during production.

Thermally sensitive active substances can only be used to a limited extent in the system in the case of matrices or therapeutic systems which have to be thermally treated and which are produced with heat treatment stages.

Attempts have already been made to introduce pure active substance in fine-crystalline form into a pressure sensitive adhesive polymer, so that the finely divided, fine-crystalline active substance dissolves with time as depot crystals in the adhesive matrix layer (DE-OS 35 00 508=U.S. Pat. No. 4,719,226). This process is not suitable for volatile and thermally sensitive active substances, because it includes thermal treatment stages.

Another attempt to increase the capacity of such therapeutic systems comprises embedding in a pressure sensitive adhesive layer of such a system active substance depots in the form of microcapsules, which are surrounded by a control membrane (see U.S. Pat. Nos. 3,598,123 and 3,731, 683). The production of such control membrane-surrounded microcapsules is extremely complicated and expensive and cannot be performed for many active substances. The mixing of the active substance-containing microcapsules under a reservoir material constitutes a further difficult process stage, during which the micro-capsules can easily be damaged or destroyed, which can lead to an unsatisfactory constancy of the active substance content in the finished therapeutic system. The process of U.S. Pat. No. 3,598,123 is difficult to perform for liquid active substances, particularly if the liquid substance is present in readily volatile form.

German patent 3 424 837 discloses a depot plaster, which can be used for liquid materials and has a covering film, a liquid active substance in an outwardly bulging region of the covering film and a control membrane covering the active substance and permeable for the latter. Between the covering film and the control membrane is provided an active substance distribution device, namely a non-woven fabric, which uniformly distributes the active substance liquid on the control membrane and which is effective over a large surface area. In the case of the depot plaster of German patent 3 424 837 the covering film and the control membrane are welded together in their outer regions in order to prevent an outward flow of the liquid active substance.

However, the known depot plaster is disadvantageous in that the liquid therein flows freely and can easily run out if the adhesive or welded edges are damaged and also requires an expensive control membrane, which must be provided in addition to the active substance distribution device in order to kinetically control the delivery of the active substance.

The problem of the present invention is consequently to provide a novel therapeutic system with active substance depot for the administration of the active substance, which can be manufactured less expensively and more reliably than the prior art systems which is also suitable for processing volatile and/or thermally unstable components.

SUMMARY OF THE INVENTION

According to the invention this problem is solved by a therapeutic system, which is characterized in that the active substance distribution device and the active substance delivery control device are a reservoir matrix having one or more discrete active substance depots arranged in a spatially defined manner with respect to one another and having a higher active substance concentration than in the reservoir matrix. During the production of the therapeutic system, the reservoir matrix can be free from active substances and is only enriched therewith over a period of time, i.e. during the storage of the system or, in the case of highly volatile substances, during the production of the system. Thus, it is an advantage of the invention that now active substances, which are thermally unstable and/or volatile can be introduced during manufacture into transdermal systems in the form of a depot and without any thermal stressing. There is no need for stages, such as the mixing of the reservoir matrix material with the active substance, and instead said material becomes saturated with the active substance at room temperature during the storage of the therapeutic system. Production is simplified due to the omission of the production stages for the active substance-saturated matrix.

More specifically the invention is directed to a method for making a transdermal therapeutic system, comprising, (a) applying a pressure sensitive adhesive to a detachable protective layer;

(b) applying an absorbent fabric material to the pressure sensitive adhesive;

(c) applying an active substance in liquid form onto the unapplied side of the fabric material; and (d) laminating a backing layer to the fabric material, which defines the upper surface of the device and is substantially impermeable to the active substance.

Another embodiment of the invention consists in a method for preparing a transdermal therapeutic system comprising;

(a) applying a first pressure sensitive adhesive to an absorbent fabric layer;

(b) applying in liquid form an active substance to the unapplied side of the fabric layer;

(c) applying a second pressure sensitive adhesive layer to the unapplied side of the fabric layer; and (d) laminating a substantially impermeable backing to the second adhesive layer.

Due to the fact that here a reservoir matrix with its own control function is used, which is inter alia determined by the migration speed of the active substance through the matrix, there is no need to provide a control membrane, which requires additional process stages and membrane material during production. The depot can consist of pure active substance, which can be solid or fluid, but may contain also inert adjuvants. The term "inert" is here understood to mean that active substance and adjuvant do not react with one another. An "inert" adjuvant can also be a substance having physiological effects, such as e.g. dimethylsulfoxide (DMSO) or the like, which e.g. increases the permeability of the skin. Suitable adjuvants are also support materials which make the active substance depot insensitive with respect to pressure and tension application, as well as carriers. Thus, the support material may be an inert adjuvant of planar fabric material for providing and supporting a distributing function. For example, a non-woven fabric may serve as an inert adjuvant and as the supporting fabric and assist the uniform distribution of nicotine or any other active substance referred to hereafter. In other words, such fabric material will facilitate the processing of the active substance.

It is possible to use active substances which can be applied in transdermal manner and typical examples of these are given below.

Nicotine.

Corticosteroids: hydrocortisone, prednisolone, beclomethasone-propionate, flumethasone, triamcinolone, triamcinolone-acetonide, fluocinolon, fluocinolinacetonide, fluocinolon-acetonide acetate, clobetasolpropionate, etc.

Analgesics, anti-inflammatory agents: acetaminophen, mefenamic acid, flufenamic acid, diclofenac, diclofenac-sodium-alclofenac, oxyphenbutazone, phenylbutazone, ibuprofen, flurbiprofen, salicylic acid, 1-menthol, camphor, sulindac-tolmetin-sodium, naproxen, fenbufen, etc.

Hypnotically active sedatives: Phenobarbital, amobarbital, cyclobarbital, triazolam, nitrazepam, lorazepam, haloperidol, etc.

Tranquilizers: fluphenazine, thioridazine, lorazepam, flunitrazepam, chloropromazine, etc.

Antihypertensives: pindolol, indenolol, nifedipin, lofexidin, nipradinol, bucumolol, etc.

Antihypertensively acting diuretics: hydrothiazide, bendroflumethiazide, cyclopenthiazide, etc.

Antibiotics: penicillin, tetracycline, oxytetracycline, fradiomycin sulfate, erythromycin, chloramphenicol, etc.

Anesthetics: lidocaine, benzocaine, ethylaminobenzoate, etc.

Antimicrobiological agents: benzalkonium chloride, nitrofurazone, nystatin, acetosulfamine, clotrimazole, etc.

Antifungal agents: pentamycin, amphotericin B, pyrrolnitrin, clotrimazole, etc.

Vitamins: vitamin A, ergocalciferol, chlolecalciferol, octotiamine, riboflavin butyrate, etc.

Antiepileptics: nitrazepam, meprobamate, clonazepam, etc.

Coronary vasodilators: dipyridamole, erythritol tetranitrate, pentaerythritol tetranitrate, propatylnitrate, etc.

Antihistamines: diphenyl hydramine hydrochloride, chlorpheniramine, diphenylimidazole, etc.

Antitussives: dertromethorphan (hydrobromide), terbutaline (sulphate), ephedrine (hydrochloride), salbutamol (sulphate), isoproterenol (sulfate, hydrochloride), etc.

Sexual hormones: progesterone, etc.

Thymoleptics: doxepin, etc.

Further medicaments/pharmaceuticals: 5-fluorouracil, fentanyl, desmopressin, domperdon, scopolamine (hydrobromide), peptide, etc.

Obviously, this list is not exhaustive.

Advantageously the active substance reservoir matrix can be built up in layer form, the layers being the same or different. The reservoir matrix can be pressure sensitive adhesive and can e.g. be a rubber material, such as styrene/isoprene/styrene block copolymers, silicone rubber or synthetic resins, such as poly(meth)acrylate, polyurethane, polyvinylether, polyester, etc.—a list of suitable matrix materials appearing e.g. in DE-OS 35 00 508, corresponding to U.S. Pat. No. 4,719,226, which is incorporated by reference. It can be advantageous if the reservoir matrix is pressure sensitive adhesive, because this can obviate the need for providing a separate pressure sensitive adhesive fixing device in the system. The use of such a pressure-sensitive adhesive matrix is inter alia dependent on the compatibility of the matrix material with the active substance. Pressure sensitive adhesive matrix materials are known.

Preferred non-pressure sensitive adhesive matrix materials are polymers comprising poly(meth)acrylate, polyvinylpyrrolidone, ethylcellulose, hydroxypropylcellulose, hydroxypropylmethylcellulosephthalate, polyvinylalcohol or copolymers thereof with vinyllaurate or maleic acid, vinylacetate or copolymers thereof with vinyllaurate or maleic acid, polyvinylether, butylrubber and polycaprolactam.

For example, the active substance depot or depots can be introduced between a backing side reservoir matrix layer and a skin side reservoir matrix layer, the thickness ratio of the reservoir matrix layers preferably being between approximately X:Y=1:1 and 1:20 and in particularly preferred manner 1:1 and 1:5.

It can be appropriate in other cases if the reservoir matrix or reservoir matrix layers from which said matrix is formed, to be provided at least on one side with pressure sensitive adhesive coatings.

According to a further advantageous development of the inventive system, the active substance depot can be arranged between the reservoir matrix and the backing layer, which is e.g. suitable for solid active substances which may be applied in the form of a corpuscle.

In a preferred embodiment of the invention the fixing device can be formed by adhesive portions embedded in the reservoir matrix, such as e.g. an all-round adhesive edge or adhesion points.

In conventional manner, it is possible to provide a detachable protective layer for the surfaces of the therapeutic system facing the skin.

The sum of the active substance in the depot and reservoir matrix is advantageously up to 20 times the therapeutically necessary active substance quantity.

A particularly preferred process for producing such systems comprises the reservoir matrix being formed from two reservoir matrix layers, which can be the same or different, between which is introduced the active substance depot. The reservoir matrix layers can be joined together by the application of pressure and/or heat. The depot can also be introduced into the reservoir matrix under pressure application, e.g. by injecting, for example, through a hypodermic syringe, a predetermined quantity or pressing in an active substance corpuscle into a soft matrix layer.

A further preferred process is forming at least part of the therapeutic system by strewing on particles.

It is also possible to produce a multilayer active substance matrix. The covering and reservoir matrix layer can also be joined by heat or pressure. The reservoir matrix layer or layers can at least partly be produced from liquid materials, e.g. from a dispersion, a melt or solutions.

The inventive therapeutic system is in particular suitable for local or systemic transdermal active substance application in human or veterinary medicine or can also be used in cosmetics.

BRIEF DESCRIPTION OF THE DRAWINGS

The invention is described in greater detail hereinafter relative to non-limitative embodiments of the inventive therapeutic system and the attached diagrammatic drawings, which show.

DETAILED DESCRIPTION OF THE INVENTION

Figure 1:
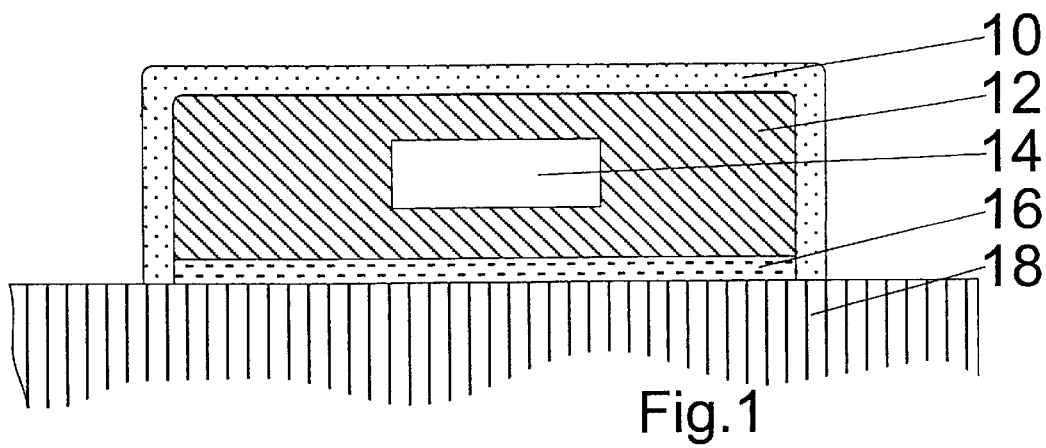
FIG. 1 is a section through a preferred embodiment of an inventive therapeutic system.

FIG. 1 is a section through an inventive therapeutic system, which is fixed to the skin 18 by a fixing device 16, e.g. a porous pressure sensitive adhesive layer or the like. On fixing device 16 is located reservoir matrix 12 which, at the time of production, is preferably free from active substance (active substance saturation taking place during storage). In the reservoir matrix 12 is embedded a depot 14, which is represented here as a solid active substance which dissolves in the reservoir matrix material 12 and is supplied to the skin 18 by fixing device 16. The therapeutic system is sealed to the outside by a backing layer 10, which is impermeable for the active substance and preferably also moisture and simultaneously has a support function for the system.

Figure 2:
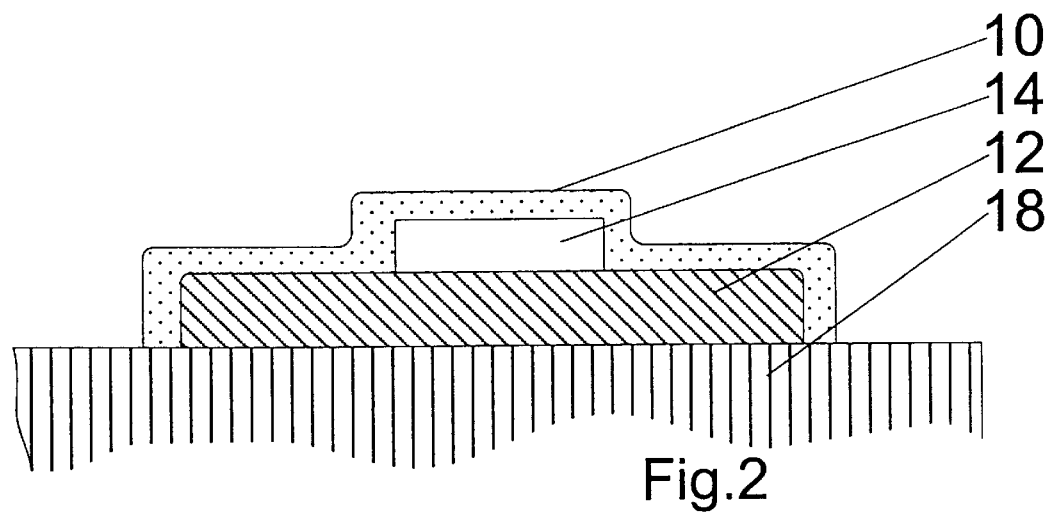
FIG. 2 is a section through a further preferred embodiment of a therapeutic system, in which the active substance depot is located between the backing layer and the reservoir matrix.

FIG. 2 shows another variant of the inventive system, in which an active substance depot 14 is located on a reservoir matrix layer 12 and is covered by a backing layer 10. The fixing device is not shown in this drawing and can e.g. be a pressure sensitive adhesive border or edge or the like, which applies the skin contact surface of the therapeutic system closely to skin 18. This embodiment of the invention is advantageous in that its production is very simple. It is merely necessary to apply clearly defined quantities of active substance, in the form of a solid or a viscous liquid to the prefabricated matrix layer 12 and to seal or terminate the same by a backing layer 10.

The process for producing the system according to FIG. 2 is less expensive than for that according to FIG. 1. However, it can only be used if it is not absolutely necessary that active substance 14 is enclosed on all sides by matrix 12, e.g. due to the volatility of active substance 14 or due to a necessarily large contact surface between active substance 14 and reservoir matrix 12. It is e.g. advantageous for substances which very readily dissolve in active substance 14 reservoir and without difficulty diffuse in it, so that there is no need for a large contact surface between active substance 14 and active substance reservoir matrix 12.

Figure 3:
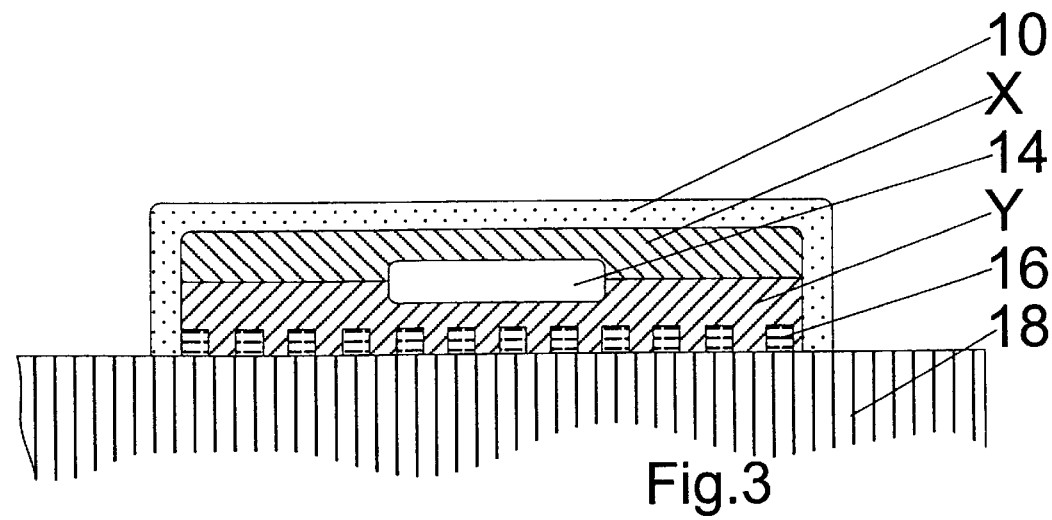
FIG. 3 is a section through a further preferred embodiment of the inventive system, wherein the active substance reservoir is embedded between matrix layers.

FIG. 3 shows another preferred embodiment, in which an inventive therapeutic system is fixed to the skin 18 by means of adhesive particles or portions 16 embedded on the skin 18 side in the active substance reservoir matrix material. The active substance reservoir layer 12 here comprises an upper layer X and a lower layer Y, between which is introduced the active substance, which is e.g. here in liquid form. The provision of two reservoir matrix layers X, Y is advantageous if a system is being produced in such a way that firstly the lower active substance reservoir layer Y is provided, optionally with an already coated on covering film or the like and then in accordance with a predetermined pattern the active substance/material is applied, the next active substance reservoir layer X is superimposed, and finally in conventional manner the backing layer 10 or optionally various adhesive layers 16 are applied to complete the system. It may also be appropriate to firstly place the two active substance reservoir layers X, Y on top of one another, then inject a predetermined quantity of active substance between the two reservoir layers X, Y and in this way keep evaporation of the active substance 14 to a minimum.

Figure 4:
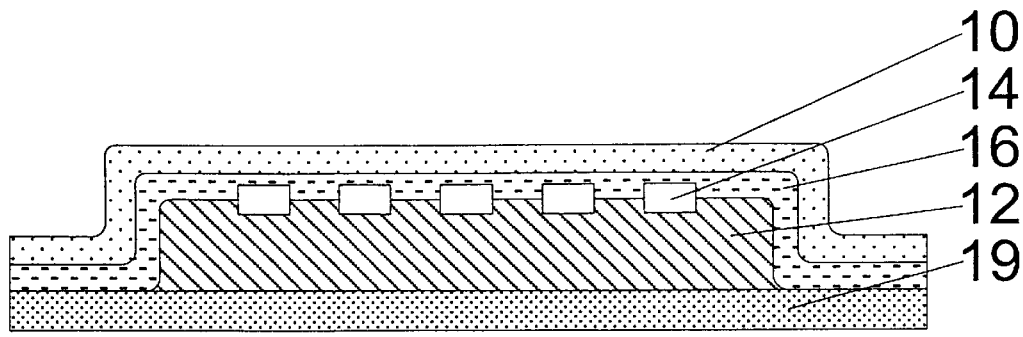
FIG. 4 is a section through an inventive therapeutic system with several active substance depots arranged in one plane.

FIG. 4 shows an embodiment of an inventive transdermal system with several active substance depots 14 arranged in one plane and placed between a pressure sensitive adhesive layer 16 and a reservoir matrix 12, layer 16 simultaneously fixing the backing layer 10 to the transdermal system. The transdermal system is sealed by a detachable protective layer 19.

Figure 5:
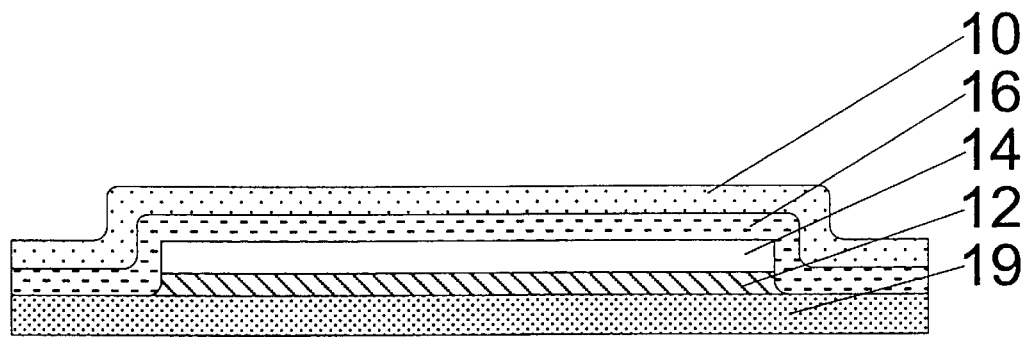
FIG. 5 is a section through an inventive therapeutic system with an active substance depot in layer form.

FIG. 5 shows another embodiment of an inventive transdermal system, in which a backing layer 10 is coated on one side with an adhesive layer 16 and on it is located active substance 14, optionally with adjuvants, such as material for facilitating processing of active substance 14 (e.g. tabletting aids) or carriers, like fabrics and the like. To the flat active substance depot 14 is applied a reservoir matrix 12 which is in turn covered by a detachable protective film.

Figure 6:
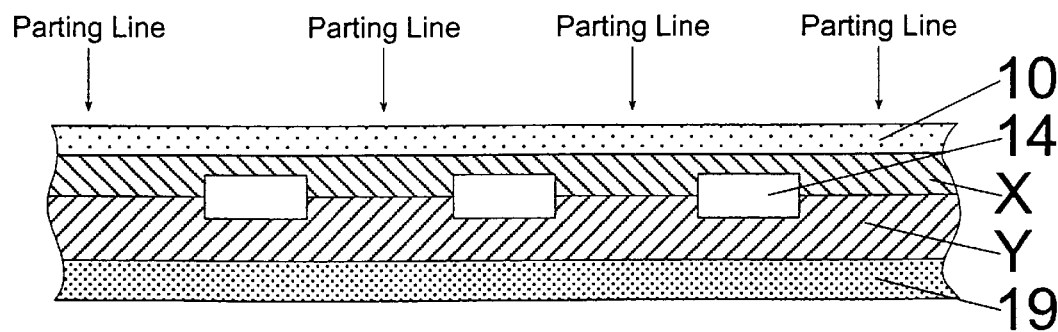
FIG. 6 is a section through a web-like semifinished product according to the invention.

FIG. 6 shows the precursor of an inventive transdermal system, such as is obtained during a preferred production process. A web-like protective coating material 19, such as e.g. waxed paper or the like is covered by a reservoir matrix layer Y, which is here constructed in pressure sensitive adhesive manner and on same are located in accordance with a predetermined pattern of active substance depot bodies 14.

Matrix layer Y is covered by a second matrix layer X, which can e.g. comprise a material differing from that of layer Y. The second matrix layer X is sealed by a backing film 10. Along the arrows are located the parting or separating lines, along which the intermediate product is cut or punched during the production of the inventive transdermal systems and then prepared in the usual way.

Typical thicknesses for inventive transdermal systems are in the case of a total thickness of approximately 123 to 5550 $\mu$m, preferably 285 to 1550 $\mu$m; thickness of the backing layer 8 to 150 $\mu$m and preferably 15 to 100 $\mu$m; thickness of the reservoir 100 to 5000 $\mu$m, preferably 200 to 1330 $\mu$m; thickness of the protective layer 15 to 400 $\mu$m, preferably 70 to 150 $\mu$m.

For special application it is also possible to market the "semifinished product" as such, so as to enable users to carry out the separation of the systems, so that the semifinished product acts in the manner of a "storage pack".

Preferred examples of the invention are described below.

EXAMPLE 1

Production of a Nicotine Plaster

Nicotine plasters, such as are used to stop people from smoking, are, according to the invention, produced as follows.

A pressure sensitive adhesive material comprising 2.0825 kg of a 40% solution of a self-crosslinking acrylate copolymer, e.g. of 2-ethyl-hexyl acrylate, vinyl acetate, acrylic acid and titanium chelate ester or DUROTAC 280-2416 of the firm National Starch/Chemical B.V. in a mixture of ethyl acetate, ethanol, hexane and methanol, 147 g of an acrylic resin of dimethylaminoethylmethacrylate and neutral methacrylate (EUDRAGIT E 100 of the firm of RÖHM PHARMA), as 20 g of a mixed acidic triglyceride of fractionated $C_8$–$C_{10}$coconut fatty acids (Miglyol 812 of the firm Dynamit Nobel) are applied to a protective layer vapor-deposited with aluminum on one side and abhesively finished on both sides and the solvent is evaporated at 50 to 80° C. An approximately 300 g/m$^2$ layer is obtained. From the thus produced pressure sensitive adhesive layer are punched round discs with a diameter of 65 mm. The projecting edges are worked and central to the same is applied in each case one circular disc of a non-woven fabric e.g. fibrous mixture of viscose staple cotton fiber 50:50 with a substance weight of 80 g/m$^2$ and with a diameter of 40 mm. An example of such a product is PARATEX II/80, a product of LOHMANN GMBH & CO KG. PARATEX is a registered trademark of Lohmann GmbH & Co. KG. To this is applied nicotine as the active substance in solution (140 g nicotine in 100 g of an acrylic resin of dimethylaminoethylmethacrylate and neutral methacrylates (EUDRAGIT E 100 of the Firm RÖHM PHARMA) in 102 mg doses/disc. The thus produced patches are immediately laminated with a nicotine impermeable backing layer (a 15 $\mu$m thick polyester film on one side of which aluminum is vapor deposited), and sealed in four-edge sealing bags of a suitable packing material.

In this case the non-woven fabric serves as the supporting fabric and to assist the uniform distribution of the nicotine as an inert adjuvant as defined hereinbefore.

Due to the fact that, according to the invention, an active substance solution can be rapidly applied to a matrix layer and is then covered by an active substance impermeable covering layer, it is possible for the first time to obtain in a satisfactory manner well dosed nicotine plasters.

Nicotine Release Test (in Vitro)

A nicotine plaster produced according to Example 1 after removing the protective layer is immersed in 80 ml of isotonic common salt solution at 37° C. and the released nicotine quantity is determined liquid chromatographically after predetermined intervals. The release medium volume was chosen in such a way that "sink" conditions are obtained over the entire test period. The following results were obtained:

Nicotine released in vitro per plaster:

after 2 hours: 23.90 mg/plaster after 4 hours: 32.34 mg/plaster after 8 hours: 41.50 mg/plaster after 24 hours: 56.54 mg/plaster

EXAMPLE 2

Production of a Nicotine Plaster

Another nicotine plaster according to the invention may be inventively produced as follows:

A pressure sensitive adhesive material (adhesive 1) comprising 1.9758 kg of a 40% solution of a self-crosslinking acrylate copolymer (DUROTAC 280-2416 of the firm Delft National & Chemical B.V.) in a mixture of ethyl acetate, ethanol, heptane and methanol, 189.7 g of an acrylic resin of dimethylaminoethylmethacrylate and neutral methacrylate (EUDRAGIT E 100 of the firm RÖHM PHARMA), and 20 g of a mixed acidic triglyceride of fractionated $C_8$–$C_{10}$ coconut fatty acids (Miglyol 812 of the firm Dynamit Nobel) are applied to a protective layer vapor-deposited with aluminum on one side and abhesively finished on both sides and the solvent is evaporated at 50 to 80° C. An approximately 440 g/m$^2$ layer is obtained. From the thus produced pressure sensitive adhesive layer are punched round discs with a diameter of 51 mm. The projecting edges are worked and central to the same is applied in each case one circular disc of a non-woven fabric (fibrous mixture of viscose staple fibre/cotton 70:30 with a substance weight of 40 g/m$^2$— PARATEX III/40 of LOHMANN GMBN & CO KG) and with a diameter of 42 mm. To this is applied nicotine as the active substance in solution (140 g nicotine in 100 g of an acrylic resin of dimethylaminoethylmethacrylate and neutral methacrylates—EUDRAGIT E 100 of the Firm ROHM PHARMA) in 46 mg doses/disc. The thus produced patches are immediately laminated with a nicotine impermeable backing layer (a 15 $\mu$m thick polyester film on one side of which aluminum is vapor-deposited having an approximately 110 g/m$^2$ coating of adhesive 1) and sealed in four-edge sealing bags of conventional suitable composite packing material.

In this case the non-woven fabric serves as the supporting fabric and to assist the uniform distribution of the nicotine as an inert adjuvant as defined hereinbefore.

Due to the fact that, according to the invention, an active substance solution can be rapidly applied to a matrix layer and is then covered by an active substance impermeable covering layer, it is possible for the first time to obtain in a satisfactory manner well dosed nicotine plasters.

Nicotine Release Test (in Vitro)

A nicotine plaster produced according to Example 2 after removing the protective layer is immersed in 80 ml of isotonic common salt solution at 37° C. and the released nicotine quantity is determined liquid chromatographically after predetermined intervals. The release medium volume was chosen in such a way that "sink" conditions are obtained over the entire test period. The following results were obtained:

after 2 hours: 5.1 mg/plaster after 4 hours: 7.2 mg/plaster after 8 hours: 10.1 mg/plaster after 24 hours: 16.5 mg/plaster It is to be understood that the invention is not limited to nicotine plasters and the production thereof with the claimed build-up but that other substances as preferred substances are mentioned in the specification may be administered by this new therapeutic system.

What is claimed is:

1. In a method for making a transdermal therapeutic system comprising,
   (a) applying a pressure sensitive adhesive to a detachable protective layer;
   (b) applying an absorbent fabric material to the pressure sensitive adhesive;
   (c) applying an active substance; and
   (d) laminating a backing layer to the fabric material, which defines the upper surface of the device;
   wherein the active substance is selected from the group consisting of nicotine, lidocaine, diphenylhydramine hydrochloride, salbutamol, a sexual hormone, 5-fluorouracil, fentanyl or scopolamine, is applied in liquid form onto the unapplied side of the fabric material and the backing layer is substantially impermeable to the active substance.

2. The method of claim 1, wherein the backing layer is a laminate comprising a polyester film, aluminum and a pressure sensitive adhesive.

3. The method of claim 2, wherein the laminate comprises a polyester film, wherein on the film is vapor-deposited aluminum, and on the aluminum is a layer of pressure sensitive adhesive.

4. The method of claim 1, wherein the protective layer is vapor-deposited with aluminum on one side.

5. The method of claim 1, wherein the active substance is nicotine.

6. A method for preparing a transdermal therapeutic system comprising:
   (a) applying a first pressure sensitive adhesive to an absorbent fabric layer;
   (b) applying in liquid form an active substance to the unapplied side of the fabric layer, the active substance being selected from the group consisting of nicotine, lidocaine, diphenylhydramine hydrochloride, salbutamol, a sexual hormone, 5-fluorouracil, fentanyl or scopolamine;
   (c) applying a second pressure sensitive adhesive layer to the unapplied side of the fabric layer; and
   (d) laminating a substantially impermeable backing to the second adhesive layer.

7. The method of claim 6, wherein the backing layer is a laminate comprising a polyester film, aluminum and a pressure sensitive adhesive.

8. The method of claim 7, wherein the laminate comprises a polyester film, wherein on the film is vapor-deposited aluminum, and on the aluminum is a layer of pressure sensitive adhesive.

9. The method of claim 6, wherein the active substance is nicotine.

10. The method of claim 1, wherein the active substance is fentanyl.

11. The method of claim 6 wherein the active substance is fentanyl.

12. The method of claim 1, wherein the pressure sensitive adhesive is an acrylate copolymer adhesive.

13. The method of claim 6, wherein the pressure sensitive adhesive is an acrylate copolymer adhesive.

14. A method for making a transdermal therapeutic system as claimed in claim 1, comprising
   (a) applying a pressure sensitive acrylate copolymer adhesive to a detachable protective layer which is on one side vapor-deposited with aluminum;
   (b) applying an absorbent fabric material to the pressure sensitive adhesive;
   (c) applying an active substance in liquid form onto the unapplied side of the fabric material; and
   (d) laminating to the fabric material a polyester film on one side of which aluminum is vapor-deposited, as a backing layer which defines the upper surface of the device and is substantially impermeable to the active substance.

15. The method of claim 14, wherein the active substance is fentanyl.

16. The method of claim 15, wherein the active substance is nicotine.

17. The method of claim 15, wherein the nicotine is applied as a solution.

18. The method of claim 6, wherein the device has one or more active substance depots arranged in a spatially defined manner with respect to one another and having a higher active substance concentration in the depots than in the resin matrix.

19. A method for making a transdermal therapeutic system comprising
   (a) applying an acrylic pressure sensitive adhesive to a detachable protective layer which has been vapor-deposited with aluminum;
   (b) applying an absorbent fabric material to the pressure sensitive adhesive;
   (c) applying nicotine to the unapplied side of the absorbent fabric, the nicotine being applied as a solution in an acrylic resin; and
   (d) laminating a backing layer to the fabric material, which defines the upper surface of the device, is substantially impermeable to nicotine and is a polyester film on one side of which is vapor-deposited aluminum.

20. The method of claim 19, wherein the absorbent fabric material is a non-woven material.

21. The method of claim 20, wherein the non-woven fabric material is viscose staple/cotton fibre.

* * * * *